United States Patent
Lins

(10) Patent No.: US 9,814,494 B2
(45) Date of Patent: Nov. 14, 2017

(54) SURGICAL IMPLANT DEVICE AND SURGICAL IMPLANT INSERTION ASSEMBLY FOR THE TRANSLATION AND FUSION OF A FACET JOINT OF THE SPINE

(71) Applicant: minSURG International, Inc., Clearwater, FL (US)

(72) Inventor: Robert E. Lins, Boca Raton, FL (US)

(73) Assignee: minSURG International, Inc., Clearwater, FL (US)

( * ) Notice: Subject to any disclaimer, the term of this patent is extended or adjusted under 35 U.S.C. 154(b) by 93 days.

(21) Appl. No.: 14/556,319

(22) Filed: Dec. 1, 2014

(65) Prior Publication Data
US 2015/0088200 A1    Mar. 26, 2015

Related U.S. Application Data

(63) Continuation-in-part of application No. 13/276,058, filed on Oct. 18, 2011, now abandoned, which is a continuation-in-part of application No. 12/875,374, filed on Sep. 3, 2010, now Pat. No. 8,814,907.

(60) Provisional application No. 61/239,594, filed on Sep. 3, 2009.

(51) Int. Cl.
*A61B 17/70* (2006.01)
*A61B 17/02* (2006.01)
*A61B 17/88* (2006.01)

(52) U.S. Cl.
CPC ........ *A61B 17/7064* (2013.01); *A61B 17/025* (2013.01); *A61B 17/8866* (2013.01); *A61B 2017/0256* (2013.01)

(58) Field of Classification Search
CPC ................................................. A61B 17/1739
USPC .......................................... 606/247
See application file for complete search history.

(56) References Cited

U.S. PATENT DOCUMENTS

| | | |
|---|---|---|
| 5,800,550 A | 9/1998 | Sertich |
| 6,045,580 A * | 4/2000 | Scarborough ...... A61B 17/1637 606/247 |
| 6,110,175 A | 8/2000 | Scholl |
| 6,371,987 B1 | 4/2002 | Weiland et al. |
| 6,770,096 B2 | 8/2004 | Bolger et al. |
| 7,452,369 B2 | 11/2008 | Barry |
| 7,699,878 B2 | 4/2010 | Pavlov et al. |

(Continued)

FOREIGN PATENT DOCUMENTS

WO    WO/2006/057943 A2    6/2006

*Primary Examiner* — Jan Christopher Merene
(74) *Attorney, Agent, or Firm* — Clements Bernard Walker PLLC; Christopher L. Bernard

(57) ABSTRACT

A surgical implant device configured to be implanted in a facet joint of a spine, comprising: a substantially cylindrical central body portion; and a pair of substantially prismatic side portions extending in radially opposite directions disposed on either side of the substantially cylindrical central body portion; wherein the substantially cylindrical central body portion is configured to be disposed in a central hole formed across the facet joint and crossing a plane of an articulating surface of each of a superior facet and an inferior facet thereof; wherein each of the substantially prismatic side portions is configured to be disposed in a side hole parallel to the central hole formed across the facet joint and crossing the plane of the articulating surface of each of the superior facet and the inferior facet thereof; and wherein each of the side holes partially overlap the central hole.

6 Claims, 8 Drawing Sheets

(56) References Cited

U.S. PATENT DOCUMENTS

| | | | |
|---|---|---|---|
| 7,708,761 B2 | 5/2010 | Petersen | |
| 8,070,819 B2 | 12/2011 | Aferzon et al. | |
| 8,133,261 B2 | 3/2012 | Fisher et al. | |
| 8,162,981 B2 | 4/2012 | Vestgaarden | |
| 8,197,513 B2 | 6/2012 | Fisher et al. | |
| 2001/0016775 A1* | 8/2001 | Scarborough | A61F 2/30771 623/17.16 |
| 2001/0020186 A1* | 9/2001 | Boyce | A61F 2/4455 623/17.16 |
| 2002/0128717 A1 | 9/2002 | Alfaro et al. | |
| 2003/0088251 A1 | 5/2003 | Braun et al. | |
| 2003/0097181 A1* | 5/2003 | Castro | A61B 17/1757 623/17.11 |
| 2003/0130664 A1 | 7/2003 | Boucher et al. | |
| 2003/0144736 A1* | 7/2003 | Sennett | A61B 17/1757 623/17.11 |
| 2003/0149484 A1 | 8/2003 | Michelson | |
| 2004/0015172 A1 | 1/2004 | Biedermann et al. | |
| 2004/0138751 A1 | 7/2004 | Michelson | |
| 2005/0149193 A1 | 7/2005 | Zucherman et al. | |
| 2006/0058876 A1 | 3/2006 | Mckinley | |
| 2006/0064099 A1 | 3/2006 | Pavlov et al. | |
| 2006/0111782 A1 | 5/2006 | Petersen | |
| 2006/0190081 A1 | 8/2006 | Kraus et al. | |
| 2008/0015582 A1 | 1/2008 | Dipoto et al. | |
| 2008/0046084 A1* | 2/2008 | Sledge | A61B 17/1757 623/17.16 |
| 2008/0103512 A1 | 5/2008 | Gately | |
| 2008/0132949 A1 | 6/2008 | Aferzon et al. | |
| 2008/0255622 A1 | 10/2008 | Mickiewicz et al. | |
| 2008/0255666 A1 | 10/2008 | Fisher et al. | |
| 2009/0036927 A1 | 2/2009 | Vestgaarden | |
| 2009/0076551 A1 | 3/2009 | Petersen | |
| 2009/0099601 A1 | 4/2009 | Aferzon et al. | |
| 2009/0164020 A1 | 6/2009 | Janowski et al. | |
| 2009/0234397 A1 | 9/2009 | Petersen | |
| 2009/0306671 A1 | 12/2009 | McCormack et al. | |
| 2009/0312763 A1 | 12/2009 | McCormack et al. | |
| 2010/0069912 A1 | 3/2010 | McCormack et al. | |
| 2010/0121378 A1 | 5/2010 | Malek | |
| 2010/0137910 A1 | 6/2010 | Cawley et al. | |
| 2010/0191241 A1 | 7/2010 | McCormack et al. | |
| 2010/0204795 A1* | 8/2010 | Greenhalgh | A61B 17/7064 623/17.16 |
| 2010/0234905 A1* | 9/2010 | Sledge | A61B 17/7064 606/86 A |
| 2011/0160772 A1 | 6/2011 | Arcenio et al. | |
| 2011/0230912 A1 | 9/2011 | Dennis | |
| 2012/0271351 A1* | 10/2012 | Vestgaarden | A61B 17/1604 606/247 |

\* cited by examiner

SURGICAL IMPLANT DEVICE AND SURGICAL IMPLANT INSERTION ASSEMBLY FOR THE TRANSLATION AND FUSION OF A FACET JOINT OF THE SPINE

CROSS-REFERENCE TO RELATED APPLICATION(S)

The present patent application/patent is a continuation-in-part of co-pending U.S. patent application Ser. No. 13/276,058, filed on Oct. 18, 2011, and entitled "SURGICAL IMPLANT DEVICE FOR THE TRANSLATION AND FUSION OF A FACET JOINT OF THE SPINE," which is a continuation-in-part of U.S. patent application Ser. No. 12/875,374 (U.S. Pat. No. 8,814,907), filed on Sep. 3, 2010 (issued on Aug. 26, 2014), and entitled "SURGICAL IMPLANT DEVICE FOR THE TRANSLATION AND FUSION OF A FACET JOINT OF THE SPINE," which claims the benefit of priority of U.S. Provisional Patent Application No. 61/239,594, filed on Sep. 3, 2009, and entitled "SURGICAL IMPLANT DEVICE FOR THE TRANSLATION AND FUSION OF A FACET JOINT OF THE SPINE," the contents of all of which are incorporated in full by reference herein.

FIELD OF THE INVENTION

The present invention relates generally to a novel surgical implant device and surgical implant insertion assembly for treating spinal stenosis, facet arthropathy, degenerative disc disease, disc herniation, and the like. More specifically, the present invention relates to a novel surgical implant device and surgical implant insertion assembly for the translation/distraction and subsequent stabilization/fusion of a facet joint of the spine in the treatment of such conditions.

BACKGROUND OF THE INVENTION

There are a variety of conventional surgical implant devices and methodologies for stabilizing/fusing the facet joint of the spine. Most of these devices and methodologies involve drilling a single hole between and across the articulating surfaces of the facet joint, while un-translated/non-distracted, and inserting a plug or other stabilization structure in the drilled hole. Some of these device and methodologies involve placing a bolt or other retention structure through (i.e. substantially perpendicularly across) or about the articulating surfaces of the facet joint while un-translated/non-distracted.

For example, one such surgical implant device that is disposed in holes drilled between and across the articulating surfaces of an un-translated facet joint is disclosed in U.S. Pat. No. 8,623,053 (Vestgaarden, issued Jan. 7, 2014), which provides a spinal facet fusion implant that includes an elongated main body having a distal end, a proximal end, and a longitudinal axis extending between the distal end and the proximal end. The main body has a cross-sectional profile characterized by a primary axis and a secondary axis. At least one stabilizer extends radially outwardly from the main body in the secondary axis. The main body has a length along the primary axis that is less than the combined width of the spinal facets making up a facet joint. The stabilizer has a width that is sized to make a press fit into the gap between the spinal facets making up a facet joint.

Another such surgical implant device that is disposed in a hole drilled between and across the articulating surfaces of an un-translated facet joint is disclosed in U.S. Pat. No. 8,162,981 (Vestgaarden, issued Apr. 24, 2012), which provides a spinal facet fusion implant including: an elongated body having a distal end, a proximal end, and a longitudinal axis extending between the distal end and the proximal end, the elongated body having a cross-sectional profile characterized by a primary axis and a secondary axis; and at least one stabilizer extending radially outwardly from the elongated body in the secondary axis; wherein the elongated body has a length along the primary axis which is less than the combined width of the spinal facets making up a facet joint; and further wherein the at least one stabilizer has a width which is sized to make a press fit into the gap between the spinal facets making up a facet joint.

These conventional devices and methodologies, however, suffer from a number of significant shortcomings and often fail to adequately address surgeon concerns and patient symptoms.

BRIEF SUMMARY OF THE INVENTION

It is desirable, in many applications, to translate/distract the facet joint before stabilizing/fusing it, especially in the lumbar spine. This may be accomplished, for example, by placing a surgical implant insertion assembly or tool in the facet joint and rotating it, thus displacing the articulating surfaces of the facet joint with respect to one another with a translation motion and/or a distraction motion before they are held in such configuration by a surgical implant device. Such a procedure may be carried out both left and right at each level of the spine. Further, all procedures of the present invention may be performed open, through a portal tube or the like, or percutaneously, in a minimally invasive manner via a variety of approaches.

Advantageously, such displacement increases the size of the foramen, where the nerve roots exit the central spinal canal, thus addressing foraminal stenosis, which may cause leg symptoms. Such displacement also addresses central spinal canal stenosis by unbuckling or stretching out the redundant ligamentum flavum that connect each spinal segment posteriorly. Such displacement further unloads the posterior aspect of the intervertebral disc posteriorly, and may be used to address underlying degenerative disc disease, in addition to lumbar spinal stenosis, facet arthropathy (i.e. facet arthritis), and the like.

The surgical procedures of the present invention may be performed percutaneously, in a minimally invasive manner, or through two small incisions on the back, with or without a portal tube, one on each side, or in an open manner. The goal of the surgical procedures of the present invention is to stabilize/fuse the facet joint in a desirable configuration that alleviates a given physical ailment or condition. The various surgical implant devices of the present invention may be made of machined allograft (i.e. bony) material, a surgically implantable polymeric material, a surgically implantable ceramic material, a surgically implantable metallic material, etc., and may optionally include one or more holes or bores for the impaction of another material that promotes the fusion of the superior and inferior facets of the facet joint.

In one exemplary embodiment, the present invention provides a surgical implant device configured to be implanted in a facet joint of a spine, comprising: a substantially cylindrical central body portion; and a pair of substantially prismatic side portions extending in radially opposite directions disposed on either side of the substantially cylindrical central body portion; wherein the substantially cylindrical central body portion is configured to be disposed in a central hole formed across the facet joint and crossing a plane of an articulating surface of each of a superior facet and an inferior facet thereof; wherein each of the substantially prismatic side portions is configured to be disposed in a side hole parallel to the central hole formed across the facet joint and crossing the plane of the articulating surface of each of the superior facet and the inferior facet thereof; and wherein each of the side holes partially overlap the central hole. The central body portion has a substantially circular cross-sectional shape. Optionally, each of the side portions has a substantially square or rectangular cross-sectional shape. Optionally, a lower leading edge of the central body portion has a tapered shape for aiding insertion of the surgical implant device into the central hole. A lower leading edge of each of the side portions has a tapered shape for aiding insertion of the surgical implant device into the side holes. The central hole and side holes are formed across the facet joint subsequent to translation of the articulating surfaces of the superior facet and the inferior facet with respect to one another. It should be noted that, as used herein, "hole" refers to any recess of any shape formed by any means, not simply a drilled circular channel. This definition applies equally to all embodiments.

In another exemplary embodiment, the present invention provides a surgical method for implanting a surgical implant device in a facet joint of a spine, comprising: forming a central hole across the facet joint and crossing a plane of an articulating surface of each of a superior facet and an inferior facet thereof; forming a pair of side holes parallel to the central hole across the facet joint and crossing the plane of the articulating surface of each of the superior facet and the inferior facet thereof; wherein each of the side holes partially overlap the central hole; and disposing a surgical implant device in the central hole and side holes, wherein the surgical implant device comprises: a substantially cylindrical central body portion, wherein the substantially cylindrical central body portion is disposed in the central hole; and a pair of substantially prismatic side portions extending in radially opposite directions disposed on either side of the substantially cylindrical central body portion, wherein the substantially prismatic side portions are disposed in the side holes. The central body portion has a substantially circular cross-sectional shape. Optionally, each of the side portions has a substantially square or rectangular cross-sectional shape. Optionally, a lower leading edge of the central body portion has a tapered shape for aiding insertion of the surgical implant device into the central hole. A lower leading edge of each of the side portions has a tapered shape for aiding insertion of the surgical implant device into the side holes. The surgical method also comprises translating the articulating surfaces of the superior facet and the inferior facet with respect to one another prior to forming the central hole and side holes across the facet joint.

In a further exemplary embodiment, the present invention provides a surgical implant insertion assembly for implanting a surgical implant device in a facet joint of a spine, comprising: an optional guide portion configured to be partially disposed within the facet joint, thereby locating the facet joint; a translation portion configured to securely engage the superior facet and the inferior facet of the facet joint and selectively rotate about the guide portion and/or a central axis, thereby translating articulating surfaces of the superior facet and the inferior facet with respect to one another; and a cannulated retention portion disposed about the translation portion and configured to selectively engage the facet joint and selectively secure the superior facet and the inferior facet of the facet joint in a translated configuration; wherein the cannulated retention portion defines an internal bore through which holes are formed in the superior facet and the inferior facet and a surgical implant device is inserted into the facet joint once one or more of the guide portion and the translation portion are removed from the cannulated retention portion. The guide portion comprises one of an independent guide wire and a sharpened point coupled to an end of the translation portion. The translation portion comprises a pair of opposed staple-like blade structures coupled to an end of the translation portion for securely engaging the superior facet and the inferior facet. The retention portion comprises a pair of opposed protruding structures coupled to an end of the retention portion for engaging the facet joint. The retention portion also comprises a plurality of spike structures coupled to an end of the retention portion for engaging the facet joint and securing the superior facet and the inferior facet of the facet joint in the translated configuration. The internal bore of the retention portion comprises a central lobe and a pair of opposed side lobes partially intersecting the central bore. The internal bore of the retention portion has a shape that substantially matches the shape of the surgical implant device disposed there through.

In a still further exemplary embodiment, the present invention provides a surgical method for implanting a surgical implant device in a facet joint of a spine, comprising: translating articulating surfaces of a superior facet and an inferior facet of the facet joint with respect to one another using a surgical implant insertion assembly; securing the superior facet and the inferior facet in a translated configuration using the surgical implant insertion assembly; forming one or more holes across the facet joint and crossing a plane of an articulating surface of each of the superior facet and the inferior facet using the surgical implant insertion assembly as a guide; and disposing the surgical implant device in the one or more formed holes using the surgical implant insertion assembly as a guide. The surgical implant insertion assembly comprises: a translation portion configured to securely engage the superior facet and the inferior facet of the facet joint and selectively rotate about a central axis, thereby translating the articulating surfaces of the superior facet and the inferior facet with respect to one another; and a cannulated retention portion disposed about the translation portion and configured to selectively engage the facet joint and selectively secure the superior facet and the inferior facet of the facet joint in the translated configuration; wherein the cannulated retention portion defines an internal bore through which the one or more holes are formed in the superior facet and the inferior facet and the surgical implant device is inserted into the facet joint once the translation portion is removed from the cannulated retention portion. The translation portion comprises a pair of opposed staple-like blade structures coupled to an end of the translation portion for securely engaging the superior facet and the inferior facet. The retention portion comprises a pair of opposed protruding structures coupled to an end of the retention portion for engaging the facet joint. The retention portion also comprises a plurality of spike structures coupled to an end of the retention portion for engaging the facet joint and securing the superior facet and the inferior facet of the facet joint in the translated configuration. The internal bore of the retention portion comprises a central lobe and a pair of opposed side lobes partially intersecting the central bore. The internal bore of the retention portion has a shape that substantially matches the shape of the surgical implant device disposed there through.

BRIEF DESCRIPTION OF THE DRAWINGS

The present invention is illustrated and described herein with reference to the various drawings, in which like reference numbers are used to denote like device/assembly components or method steps, as appropriate, and in which.

DETAILED DESCRIPTION OF THE INVENTION

Figure 1:
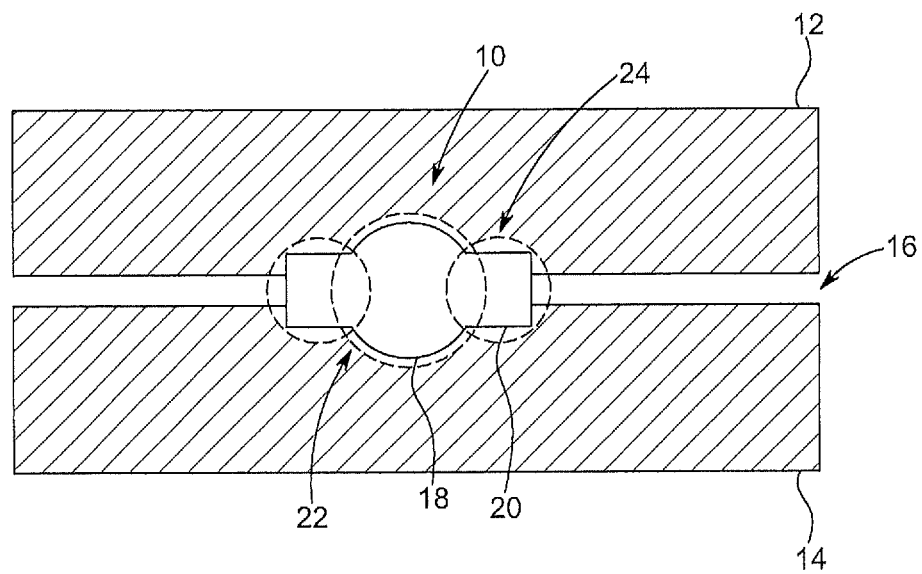
FIG. 1 is a cross-sectional end view of one exemplary embodiment of the surgical implant device of the present invention.

Referring now specifically to FIG. 1, in one exemplary embodiment of the present invention, the surgical implant device 10 is disposed generally between the superior facet 12 and the inferior facet 14 of the facet joint 16 of the spine. The surgical implant device 10 includes a body portion 18 that has a substantially circular cross-sectional shape and a pair of protruding side portions 20 each having a substantially rectangular shape that extend radially from the body portion 18. It will be readily apparent to those of ordinary skill in the art that any number of protruding side portions 20 may be used and that each may have another suitable shape. In use, the body portion 18 is disposed, or press fit, within a central hole 22 drilled in and between the superior facet 12 and the inferior facet 14; the body portion 18 breaking the plane of the associated articulating surfaces. Each of the protruding side portions 20 is disposed, or press fit, within a side hole 24 drilled in and between the superior facet 12 and the inferior facet 14; each of the side holes 24 overlapping and mating with the central hole 22; each of the protruding side portions 20 breaking the plane of the associated articulating surfaces. It will be readily apparent to those of ordinary skill in the art that, although drilled holes 22 and 24 are illustrated and described herein, appropriate recesses in the articulating surfaces of the superior facet 12 and the inferior facet 14 may be formed by other means as well. In general, it is desirable that the surgical implant device 10 is slightly larger than the holes formed to contain it, thereby creating a snug press fit. Thus, all portions 18 and 20 of the surgical implant device 10 impinge upon the purposefully excavated articulating surfaces of the superior facet 12 and the inferior facet 14 and no portions 18 and 20 are merely press fit into the natural gap of the facet joint 16. All portions 18 and 20 of the surgical implant device 10 are sized accordingly, with each of the protruding side portions 20 being substantially "thicker" than the natural gap of the facet joint 16. The surgical implant device 10 has overall dimensions on the order of several millimeters, and may be made of machined allograft (i.e. bony) material, a surgically-implantable polymeric material, a surgically-implantable ceramic material, a surgically-implantable metallic material, etc. The surgical implant device 10 may include one or more holes or bores along its major axis and/or perpendicular to its major axis for the impaction of another material that promotes the fusion of the superior and inferior facets 12 and 14 of the facet joint 16. In addition, the body portion 18 of the surgical implant device 10 may have a threaded portion or other attachment means for receiving one or more tools by which it is tamped into the facet joint 16. It should be noted that the body portion 18 and the protruding side portions 20 may be integrally formed or otherwise rigidly joined together.

Figure 2:
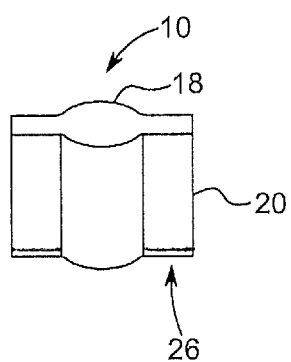
FIG. 2 is a perspective end view of one exemplary embodiment of the surgical implant device of the present invention.
Figure 3:
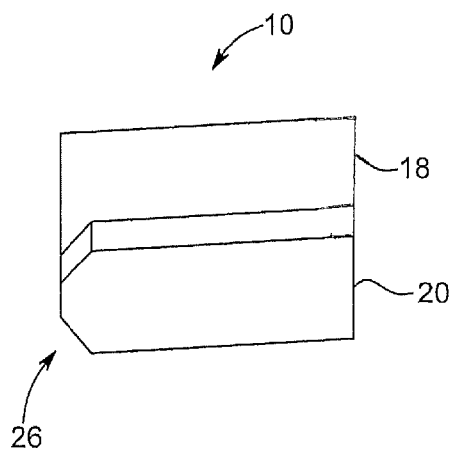
FIG. 3 is a perspective side view of one exemplary embodiment of the surgical implant device of the present invention.

Referring now specifically to FIGS. 2 and 3, the leading edge of each of the protruding side portions 20 (as well as the body portion 18) may include a point, taper, or bevel 26 to promote advancement of the surgical implant device 10 into the formed holes 22 and 24 (FIG. 1). All other edges of the surgical implant device 10 may also be beveled, as desired.

In this configuration, the surgical implant device 10 is designed to securely hold the superior facet 12 (FIG. 1) with respect to the inferior facet 14 (FIG. 1), preferably in a translated state, such that the articulating surfaces of the superior facet 12 and the inferior facet 14 may not slide with respect to one another.

Figure 4:
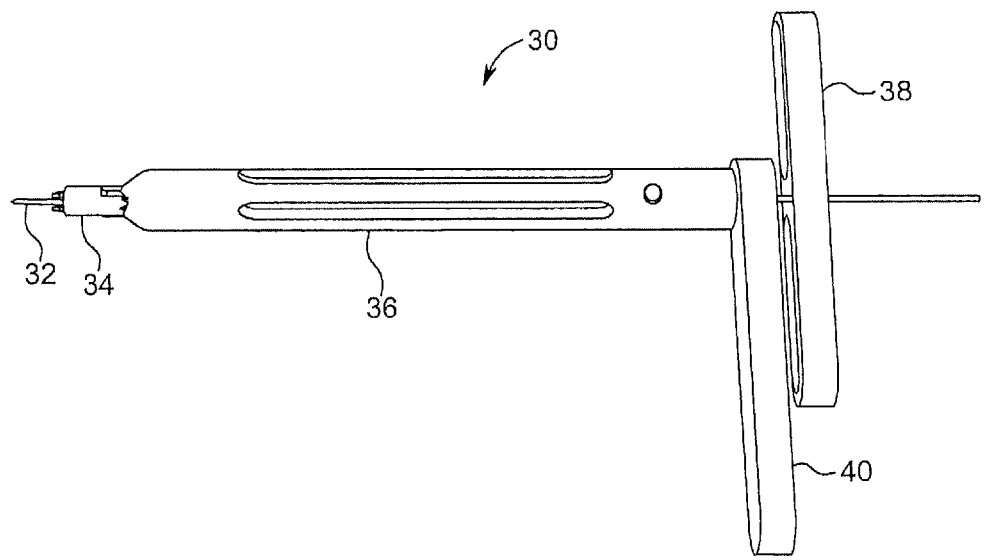
FIG. 4 is a perspective side view of one exemplary embodiment of the surgical implant insertion assembly of the present invention in a assembled state.
Figure 6:
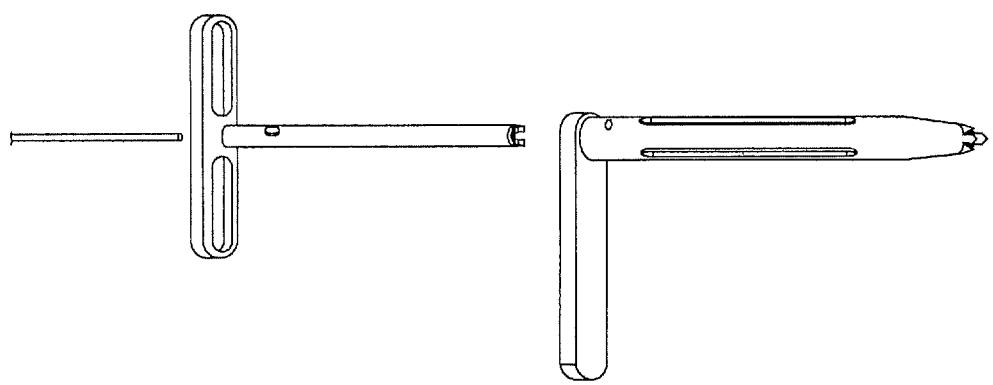
FIG. 6 is a perspective side view of one exemplary embodiment of the surgical implant insertion assembly of the present invention in a disassembled state.

Referring now specifically to FIG. 4, in one exemplary embodiment of the present invention, the surgical implant insertion assembly 30 includes a guide portion 32 configured to localize the facet joint 16 (FIG. 1) and drilling site; a cannulated translation portion 34 configured to be disposed about the guide portion 32, engage the superior facet 12 (FIG. 1) and the inferior facet 14 (FIG. 1), and rotate about the guide portion 32 to translate the articulating surfaces of the superior facet 12 and the inferior facet 14 with respect to one another prior to drilling and insertion of the surgical implant device 10 (FIGS. 1-3); and a cannulated retention portion 36 configured to be disposed about the translation portion 34 and the guide portion 32, engage the superior facet 12 and the inferior facet 14 and the facet joint 16 there between, and securely hold the superior facet 12 and the inferior facet 14 in a translated state prior to drilling and insertion of the surgical implant device 10. The guide portion 32 consists of a conventional guide wire or the like including a sharpened point that is disposed in or adjacent to the facet joint 16 such that the facet joint 16 can be localized and the translation portion 34 and the retention portion 36 can be disposed about the guide wire or the like and positioned adjacent to the facet joint 16. The translation portion 34 includes a handle portion 38 for manipulating the translation portion 34, impacting it into the facets 12 and 14, rotating it such that the facets 12 and 14 are translated, and removing it from the retention portion 36. The handle portion 38 may be disposed at any desired angle with respect to the shaft of the translation portion 34. Likewise, the retention portion 36 includes a handle portion 40 for manipulating the retention portion 36, impacting it into the facet joint 16, impacting it into the facets 12 and 14, and removing it. The handle portion 40 may be disposed at any desired angle with respect to the shaft of the retention portion 36. The guide portion 32, the translation portion 34, and the retention portion 36 are illustrated in a disassembled configuration in FIG. 6, which shows their nested cannulated configuration.

Figure 5:
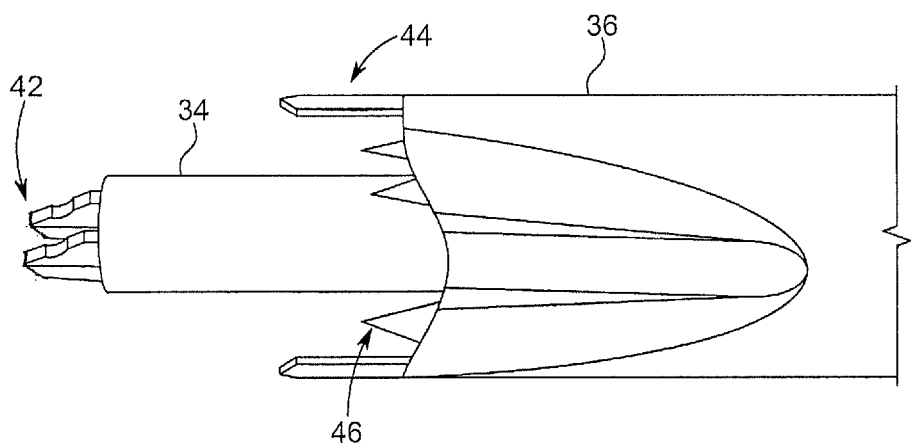
FIG. 5 is a partial perspective side view of one exemplary embodiment of the surgical implant insertion assembly of the present invention in a partially assembled state.

Referring now specifically to FIG. 5, in one exemplary embodiment of the present invention, the end portion of the translation portion 34 a pair of sharpened protrusions 42 that are configured to be selectively impacted into the superior facet 12 (FIG. 1) and the inferior facet 14 (FIG. 1) of the facet joint 16 (FIG. 1) surrounding the guide portion 32 (FIG. 4). The translation portion 34 is then rotated, rotating the sharpened protrusions 42 about the guide portion 32, thereby translating the superior facet 12 with respect to the inferior facet 14. Either before or after this translation, a pair of guide protrusions 44 are disposed within the natural gap of the facet 16, thereby securing the retention portion 36 with respect to the facet joint 16. Subsequent to the translation, a plurality of sharpened spikes 46 associated with the retention portion 36 are impacted into the translated facet 12 and 14, thereby securing the translated facets 12 and 14 in their translated configuration. At this point, the guide portion 32 and the translation portion 34 may be withdrawn from the retention portion 36, such that drilling and surgical implant device implantation may be performed through the retention portion 36.

Figure 7:
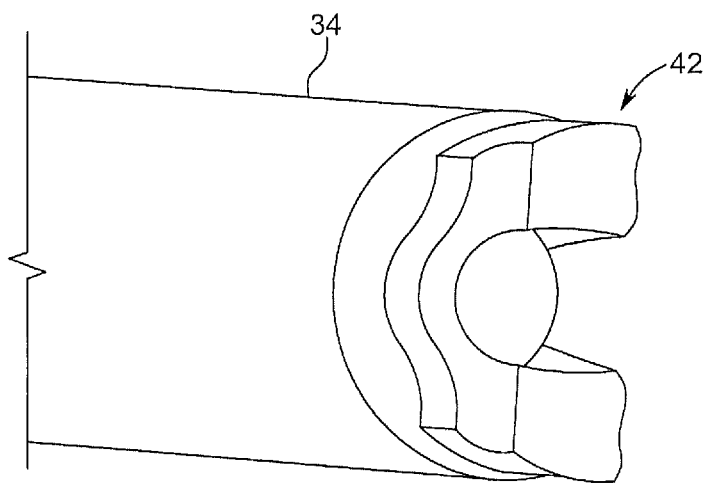
FIG. 7 is a partial perspective end view of one exemplary embodiment of the translation member of the surgical implant insertion assembly of the present invention.
Figure 8:
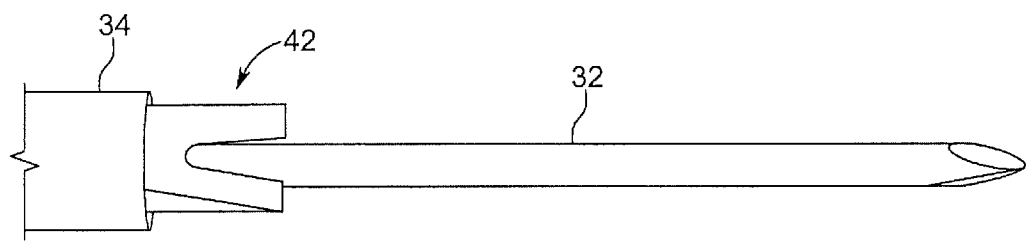
FIG. 8 is a partial perspective side view of one exemplary embodiment of the translation member and the guide member of the surgical implant insertion assembly of the present invention in an assembled state.

FIG. 7 further illustrates the configuration of the substantially cylindrical cannulated translation portion 34, including the pair of sharpened protrusions 42, which, in the exemplary embodiment illustrated, resemble sharpened staple-like blades. It will be readily apparent to those of ordinary skill in the art that other shapes may be utilized. FIG. 8 further illustrates the configuration of the substantially cylindrical cannulated translation portion 34, including the pair of sharpened protrusions 42, with the guide portion 32 disposed through the translation portion 34 and between the pair of sharpened protrusions 42.

Figure 9:
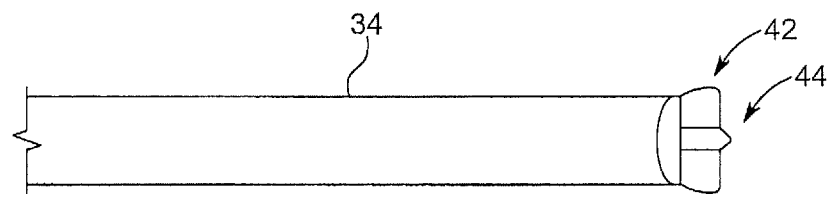
FIG. 9 is a partial perspective end view of another exemplary embodiment of the translation member of the surgical implant insertion assembly of the present invention.

Referring now specifically to FIG. 9, in another exemplary embodiment of the present invention, the substantially cylindrical translation portion 34 includes a sharpened point 44 disposed between the pair of sharpened protrusions 42, the sharpened point 44 taking the place and serving the function of the guide portion 32 (FIGS. 4, 6, and 8) and serving to localize the facet joint 16 (FIG. 1).

Figure 10:
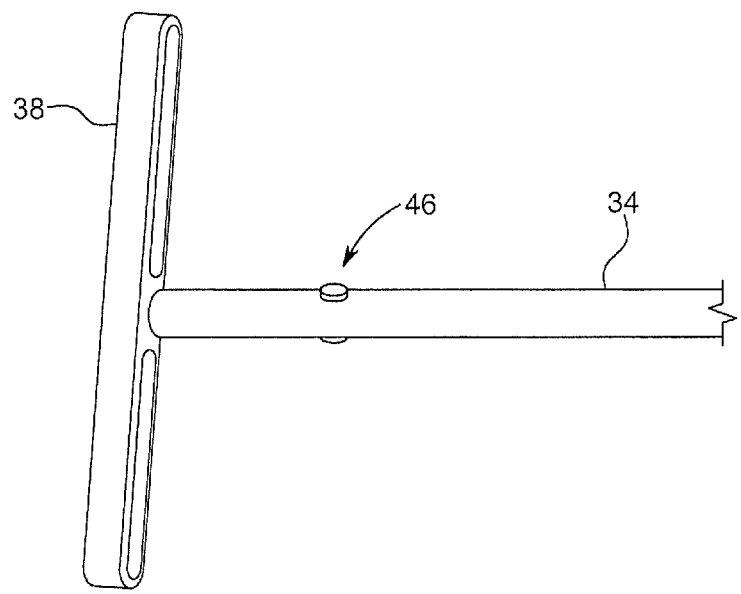
FIG. 10 is a partial perspective side view of one exemplary embodiment of the translation member of the surgical implant insertion assembly of the present invention.
Figure 11:
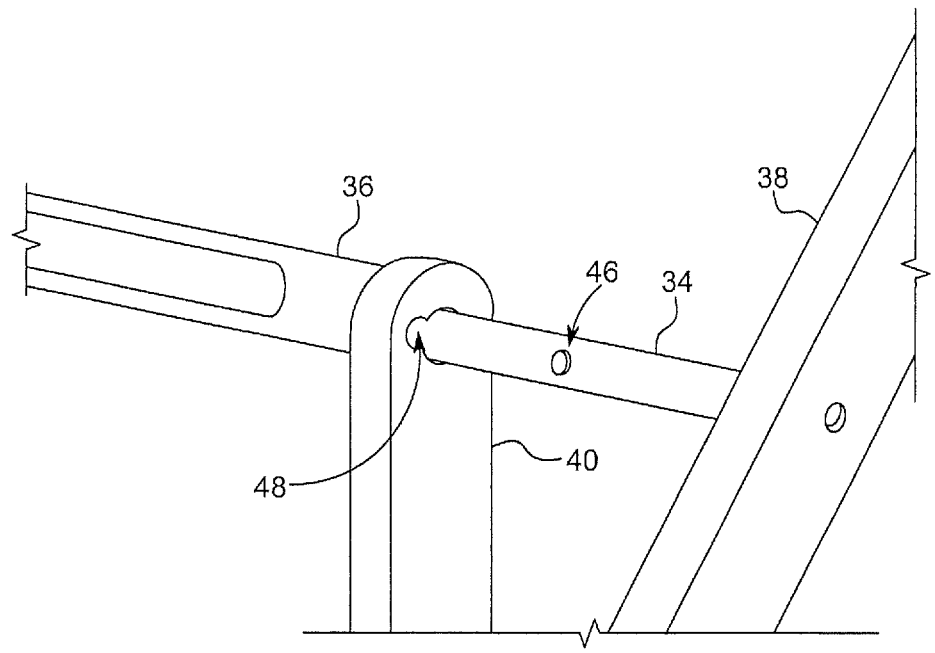
FIG. 11 is a partial perspective end view of one exemplary embodiment of the retention member and the translation member of the surgical implant insertion assembly of the present invention in a partially assembled state.

Referring now specifically to FIGS. 10 and 11, in one exemplary embodiment of the present invention, the substantially cylindrical translation portion 34 (whether cannulated or non-cannulated) includes one or more guide protrusions 46 along its shaft relatively adjacent to the handle portion 38. These guide protrusions 46 are configured to engage one or more recesses (not illustrated) manufactured into the interior bore of the substantially cylindrical cannulated retention portion 36 (FIGS. 4-6) that control and guide the depth of penetration and degree of rotation of the translation portion 34 with respect to the retention portion 36, and with respect to the facet joint 16 (FIG. 1). Essentially, the guide protrusions 46 selectively rotationally lock the translation portion 34 and the retention portion 36 together, such impaction of the surgical implant insertion assembly 30 (FIGS. 4 and 6), as a whole, may be performed, etc. FIG. 11 further highlights the insertion of the translation portion 34 and the guide protrusions 46 into the retention portion 36 via a hole 48 extending through the handle portion 40 and into the interior bore of the retention portion 36.

Figure 12:
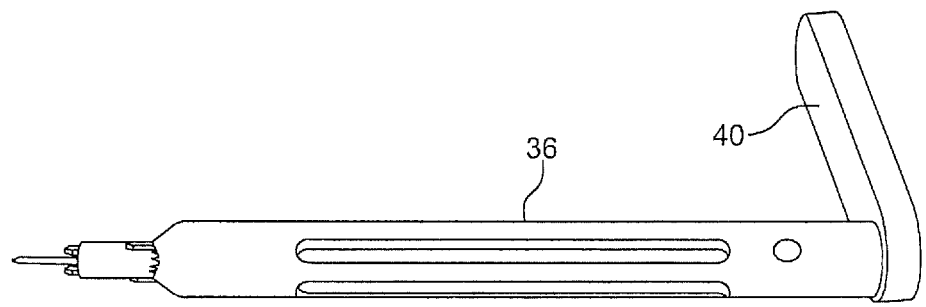
FIG. 12 is a perspective side view of one exemplary embodiment of the retention member of the surgical implant insertion assembly of the present invention.
Figure 13:
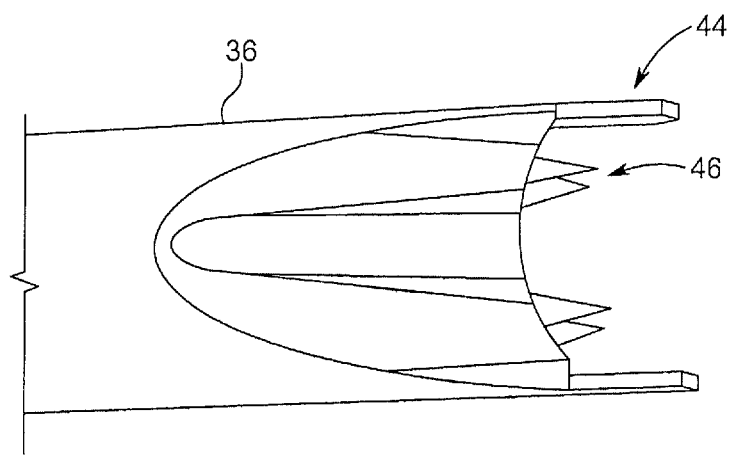
FIG. 13 is a partial perspective side view of one exemplary embodiment of the retention member of the surgical implant insertion assembly of the present invention.
Figure 14:
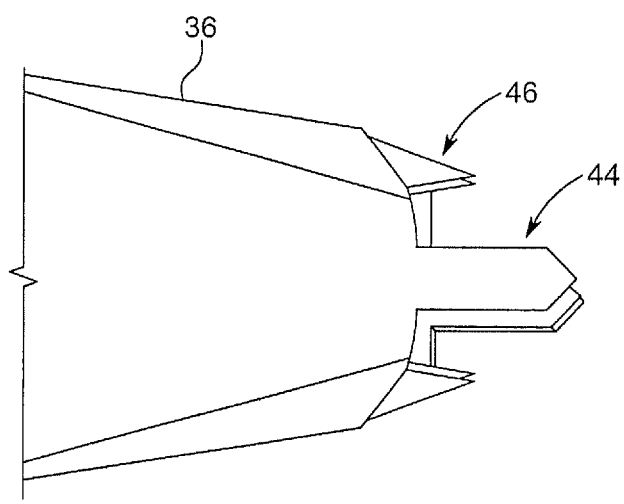
FIG. 14 is a partial perspective side view of one exemplary embodiment of the retention member of the surgical implant insertion assembly of the present invention.
Figure 15:
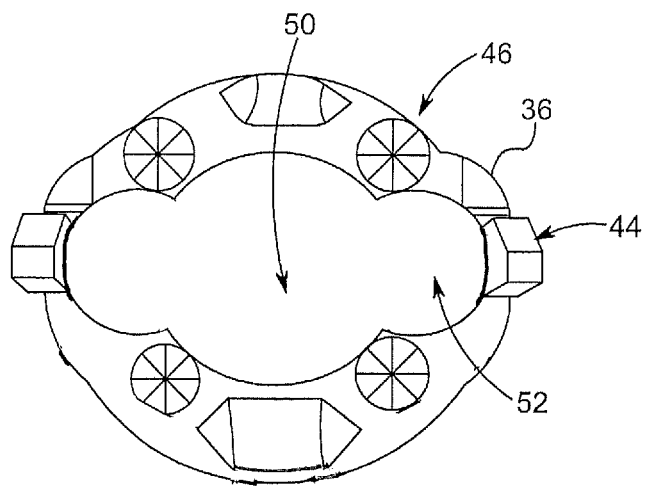
FIG. 15 is a perspective end view of one exemplary embodiment of the retention member of the surgical implant insertion assembly of the present invention.

FIG. 12 further highlights the design of the retention portion 36 and handle portion 40, and FIGS. 13-15 further highlight the design of the guide protrusions 44 and sharpened spikes 46 of the retention portion 36.

Referring now specifically to FIG. 15, in one exemplary embodiment of the present invention, once the guide portion 32 (FIGS. 4, 6, and 8) and translation portion 34 (FIGS. 4-11) are removed from the central bore 50 of the retention portion 36, successive drillings are performed through the central bore 50 and two partially overlapping side bores 52 of the retention portion 36 to form the central hole 22 (FIG. 1) and side holes 24 (FIG. 1) in the superior and inferior facets 12 and 14 (FIG. 1) in which the surgical implant device 10 (FIGS. 1-3) is then impacted into through the retention portion 36, before the retention portion is disengaged from the facet joint 16 (FIG. 1) and removed. It will be readily apparent to those of ordinary skill in the art that minor variations to this drilling pattern may be utilized.

Figure 16:
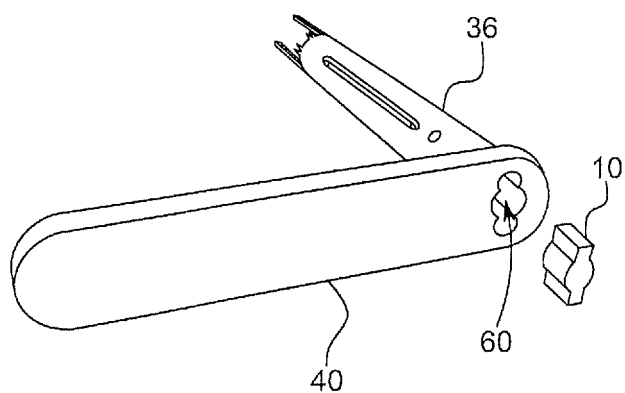
FIG. 16 is a perspective end view of one exemplary embodiment of the retention member of the surgical implant insertion assembly and the surgical implant device of the present invention in a disassembled state.

FIG. 16 more clearly illustrates the drill guide 60 of the retention portion 36 and the associated handle portion 40, defining a central drilling lobe and two overlapping side lobes, all of which intersect a portion of the superior facet 12 and the inferior facet 14.

In an alternative exemplary embodiment, the present invention provides a surgical method for implanting a surgical implant device in a facet joint of a spine, including: one or more of distracting (i.e. separating) and translating articulating surfaces of a superior facet and an inferior facet of the facet joint with respect to one another; forming one or more holes or recesses across the facet joint and crossing a plane of the articulating surface of each of the superior facet and the inferior facet thereof; and disposing a surgical implant device in the one or more holes or recesses to secure the facet joint in one or more of a distracted configuration and a translated configuration. It should be noted here that distracting the facet joint will result in translation of the facet joint. The one or more of distracting and translating the articulating surfaces of the superior facet and the inferior facet are performed using one or more of a keel structure (as described above), a clamp device disposed on one or more of the superior facet and the inferior facet, and a separation structure disposed between the superior facet and the inferior facet. This surgical method may be performed using an open surgical approach.

Although the present invention is illustrated and described herein with reference to preferred embodiments and specific examples thereof, it will be readily apparent to those of ordinary skill in the art that other embodiments and examples may perform similar functions and/or achieve like results. All such equivalent embodiments and examples are within the spirit and scope of the present invention, are contemplated thereby, and are intended to be covered by the following claims.

What is claimed is:

1. A surgical method for implanting a surgical implant device in a facet joint of a spine, comprising:

forming, through a retention tube engaging the facet joint, a central hole across the facet joint and crossing a plane of an articulating surface of a superior facet thereof and also crossing a plane of an articulating surface of an inferior facet thereof;

forming, through the same retention tube engaging the facet joint, a pair of side holes parallel to the central hole across the facet joint and crossing the plane of the articulating surface of the superior facet thereof and also crossing the plane of the articulating surface of the inferior facet thereof;

wherein each of the side holes partially overlap the central hole to form a partially overlapping central hole and side holes and wherein the retention tube simultaneously defines corresponding parallel drill channels for the central hole and the side holes; and disposing the surgical implant device in the partially overlapping central hole and side holes, wherein the surgical implant device comprises:

a substantially cylindrical central body portion, wherein the substantially cylindrical central body portion is disposed in the central hole; and a pair of substantially prismatic side portions extending in radially opposite directions disposed on either side of the substantially cylindrical central body portion, wherein the substantially prismatic side portions are disposed in the side holes.

2. The surgical method of claim 1, wherein the central body portion has a substantially circular cross-sectional shape.

3. The surgical method of claim 1, wherein each of the side portions has a substantially square, rectangular, or triangular cross-sectional shape.

4. The surgical method of claim 1, wherein a lower leading edge of the central body portion has a tapered shape for aiding insertion of the surgical implant device into the central hole.

5. The surgical method of claim 1, wherein a lower leading edge of each of the side portions has a tapered shape for aiding insertion of the surgical implant device into the side holes.

6. The surgical method of claim 1, further comprising translating the articulating surfaces of the superior facet and the inferior facet with respect to one another prior to forming the central hole and side holes across the facet joint.

* * * * *